United States Patent [19]

Latham, Jr.

[11] 4,300,717
[45] Nov. 17, 1981

[54] ROTARY CENTRIFUGE SEAL

[75] Inventor: Allen Latham, Jr., Jamaica Plain, Mass.

[73] Assignee: Haemonetics Corporation, Braintree, Mass.

[21] Appl. No.: 201,336

[22] Filed: Oct. 27, 1980

Related U.S. Application Data

[63] Continuation of Ser. No. 26,292, Apr. 2, 1979, abandoned.

[51] Int. Cl.³ .............................................. B04B 15/00
[52] U.S. Cl. ................................. 233/1 A; 277/96.1; 233/11
[58] Field of Search .............. 233/1 R, 1 A, 11, 23 R, 233/24, 27, 28, 34, 38, 45; 277/96.1, 96.2; 285/280, 281

[56] References Cited

U.S. PATENT DOCUMENTS

| | | | |
|---|---|---|---|
| 2,005,094 | 6/1935 | Lindgren | 233/11 X |
| 2,673,748 | 3/1954 | Shaw | 285/280 X |
| 2,858,149 | 10/1958 | Laser | 277/96.1 X |
| 2,878,992 | 3/1959 | Pickels | 233/11 |
| 3,409,213 | 11/1968 | Latham | 233/21 |
| 3,565,330 | 2/1971 | Latham | 233/1 A |
| 3,652,183 | 3/1972 | Potiharst | 277/96.2 |
| 3,770,181 | 11/1973 | Stahl | 277/96.1 |
| 3,801,142 | 4/1974 | Jones | 285/280 |

FOREIGN PATENT DOCUMENTS 908692  4/1954  Fed. Rep. of Germany ..... 277/96.1

*Primary Examiner*—Robert W. Jenkins
*Attorney, Agent, or Firm*—Hamilton, Brook, Smith & Reynolds

[57] ABSTRACT

An improved rotary centrifuge seal is disclosed of the type formed from a rotatable ring member (40) and a non-rotatable ring member (42) having a sealing face of each in contact to provide a dynamic seal between rotatable and stationary centrifuge elements. This improved seal is provided with means for entrapping solid particulate matter generated at areas of contact (44) and means for directing entrapped particles back to the area of contact where they are ingested. This prevents contamination of fluid being processed in the centrifuge with such solid particles, which is particularly important in blood-processing centrifuges.

17 Claims, 10 Drawing Figures

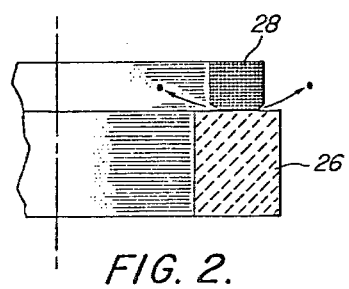
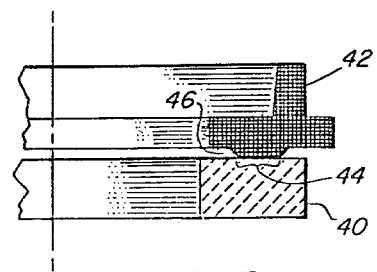
FIG. 2.  FIG. 3.
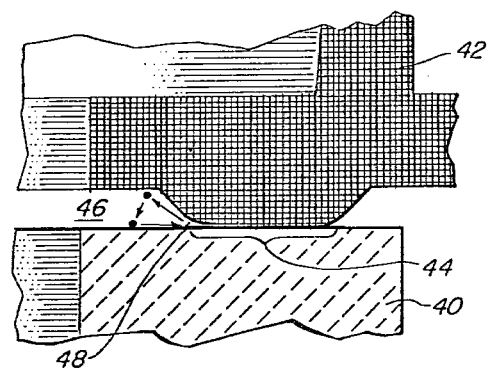
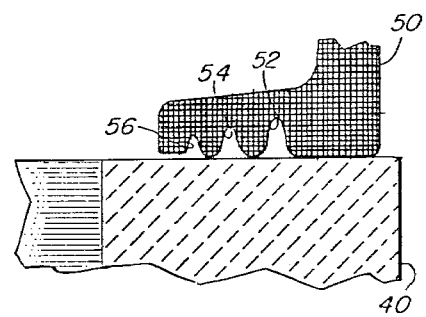
FIG. 4.  FIG. 5.
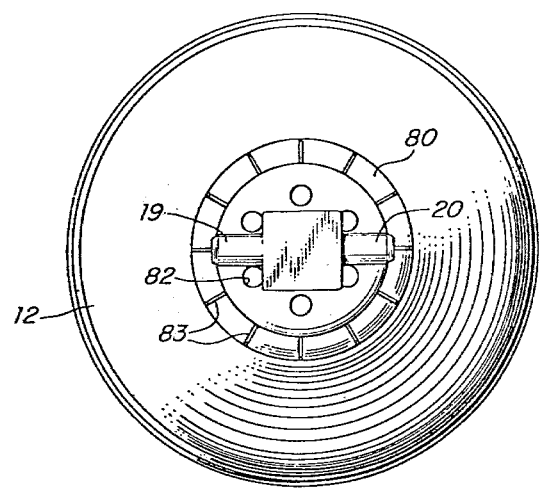
FIG. 7.

ROTARY CENTRIFUGE SEAL

This is a continuation of application Ser. No. 26,292, filed Apr. 2, 1979, now abandoned.

DESCRIPTION

TECHNICAL FIELD

This invention is in the field of centrifuges and has particular application in the field of blood processing centrifuges.

BACKGROUND ART

It is often necessary to provide an effective seal between rotatable and stationary parts of a fluid-processing centrifuge. For example, in a blood-processing centrifuge, the centrifuge bowl and associated parts often rotate while conduits making up the fluid inlet and outlet remain stationary. When processing blood, an effective rotary seal is required between these rotatable and stationary elements to insure maintenance of sterile integrity of the blood and to prevent possible contamination of the surroundings when contaminated blood is being processed.

Such a rotary centrifuge seal must be extremely efficient; must minimize leakage of air into or out of the system; must maintain frictional heating at a minimum; must provide good dissipation of heat which may be generated; must be capable of tolerating moderate misalignment and vibration between rotating and stationary parts; and must minimize production of particulate contaminants which might be introduced into the blood being processed. In addition, it is important to have a seal which is low in manufacturing cost thereby making disposability of the entire blood pathway economically feasible after a single use.

A variety of types of rotary centrifuge seals have been developed in an attempt to maximize these qualities. Some examples of rotary centrifuge seals which have proven to be successful are described in U.S. Pat. Nos. 3,409,203 and 3,565,330, issued to Latham. In these patents, rotary seals are disclosed which are formed from a stationary rigid low friction member in contact with a moving rigid member to create a dynamic seal, and an elastomeric member which provices a resilient static seal as well as a modest closing force between the surfaces of the dynamic seal.

Another rotary seal suitable for use in blood-processing centrifuges is described in U.S. Pat. No. 3,801,142 issued to Jones et al. In this seal, a pair of seal elements having confronting annular fluid-tight sealing surfaces of non-corrodable material are provided. These are maintained in a rotatable but fluid-tight relationship by axial compression of a length of elastic tubing forming one of the fluid connections to these seal elements.

Another more recently developed rotary seal has been employed in a blood-processing centrifuge known as the B. T. Bowl which is marketed by Bellco, Mirandola, Italy. In this seal, a ceramic ring member is attached to rotatable elements of the centrifuge and a fixed graphite ring is attached to stationary centrifuge elements. These ring members are in sealing relationship with each other. Additionally, an elastomeric diaphragm is attached at one end to an adapter ring for the graphite ring and at the other end to a stationary part of the centrifuge. While this type of rotary seal helps reduce passage of wear particles into the blood pathway, it lacks adequate provision for assuring that wear particles will be ingested and expelled to the outside without entry into the blood pathway.

DISCLOSURE OF INVENTION

This invention relates to a rotary centrifuge seal of the type having a rotatable ring member and a non-rotatable ring member having sealing surfaces thereof in sealing engagement with each other. More specifically, this invention comprises the improvement of providing both means for entrapping solid particulate matter on the side of the seal toward the blood pathway which may be generated at areas of contact between the two ring members during operation of the centrifuge and means for directing such entrapped particles back to the area of contact between the ring members so that such particles are ingested and expelled to the outside. In an embodiment, the means for entrapping and means for directing are provided by one or more recessed areas in the sealing surface of the fixed ring member so that an area of non-contact is formed contiguous to and radially inwardly of the area of contact. Alternative embodiments include seals having a nonrotatable ring member with an extension providing increased surface area for the dissipation of heat and/or for providing a temporary increase in torque in order to achieve breakaway in exceptional circumstances where the rotatable and non-rotatable ring members have unusual adherence to each other.

The centrifuge rotary seal can optionally be provided with a number of other features to minimize generation of solid particulate matter or to prevent such matter which may be generated from contaminating fluid being processed. For example, clearances between rotating and stationary centrifuge parts can be generously sized so that any slight misalignment which occurs during operation does not result in contact between rotating and fixed elements. This eliminates, of course, many of the potential sites where solid particulate matter could be generated. Additionally, the non-rotatable ring member can be provided with a convex radius at its inside lower corner and/or with a downwardly expanding slightly conical surface on its inner wall which will also help to direct any particulate matter generated towards the area of contact between the two ring members. A cylindrical shield also can be positioned inside the rotary seal rings attached to the rotatable ring and projecting well above the plane of the rubbing surfaces as a further way of preventing relatively large particles from reaching the fluid pathway. It may also be desirable to provide the lower ring member with a smaller inside diameter than the top ring to provide a shoulder to catch any particulate matter generated.

BRIEF DESCRIPTION OF DRAWINGS

FIG. 2 is an exploded cross-sectional view of the ring members in the rotary seal of FIG. 1 and illustrates possible trajectories of solid particles generated at areas of contact in such a seal;

FIG. 3 is a cross-sectional view of the ring members in one embodiment of an improved rotary centrifuge seal according to this invention;

FIG. 4 is an exploded view of the ring members shown in FIG. 3 illustrating the entrapment and redirection of solid particles generated at areas of contact between the ring members of this seal;

FIG. 5 is a cross-sectional view of another embodiment of an improved rotary centrifuge seal according to this invention;

FIG. 7 is a plan view of the centrifuge bowl of FIG. 6;

BEST MODE FOR CARRYING OUT THE INVENTION

Figure 1:
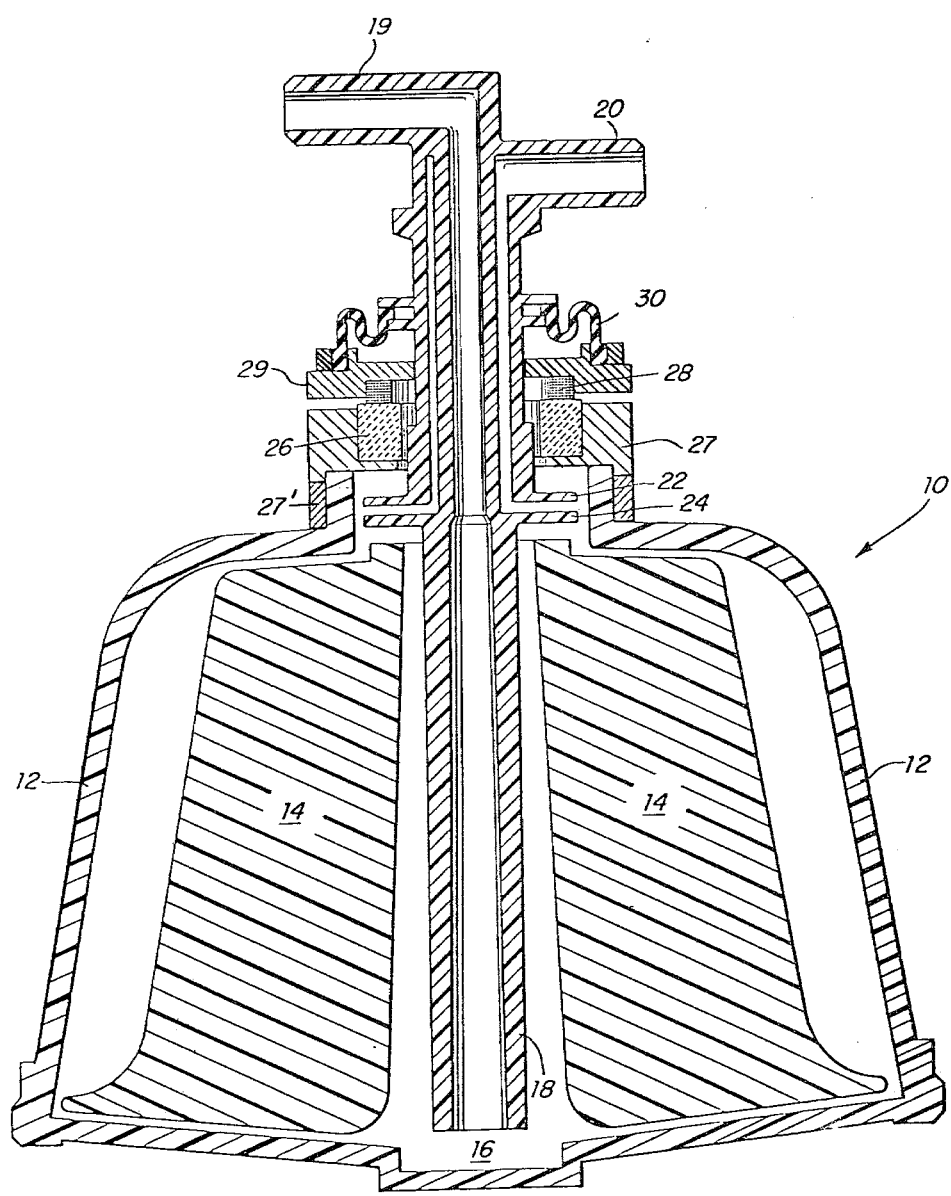
FIG. 1 is a cross-sectional elevational view of a blood-processing centrifuge having a rotary seal typical of the type used in the prior art.

FIG. 1 illustrates a blood-processing centrifuge 10 incorporating a rotary centrifuge seal of a type typically used in the prior art. As can be seen, blood-processing centrifuge 10 has a centrifuge bowl 12 which rotates around a cylindrical core section 14 during operation to separate blood into its components. Whole blood is introduced into the central port 16 located at the bottom of centrifuge 10 through feed tube 18 which extends upwardly through the center of centrifuge 10 and then makes a 90° turn at its upper end to form inlet port 19 which can be connected to blood tubing (not shown). Feed tube 18 remains stationary during operation of centrifuge 10 whereas bowl 12 spins at high speed.

Peripheral port 20 is provided to allow separated blood components to flow out of centrifuge 10. Separated components are transported to peripheral port 20 through a channel formed between upper channel-defining member 22 and lower channel-defining member 24, both of which are attached to feed tube 18.

A rotary seal is formed from rotatable ceramic ring 26 attached by adapter rings 27 and 27' which in turn are attached to centrifuge bowl 12. Fixed graphite ring 28, having a larger inside diameter and a smaller outside diameter than ring 26, rests on top of ceramic ring 26. The upper surface of ceramic rotatable ring 26 is smooth and provides a sealing surface with a similar smooth and sealing surface on the bottom of ring 28. Therefore, contact between these respective surfaces forms a dynamic seal between rotatable and stationary elements of blood-processing centrifuge 10. A secondary seal is formed from elastomeric diaphragm 30, which is locked into a keyhole slot in feed tube 18 at one end and indirectly fixed to carbon ring 28 by an adhesive joint to adapter ring 29 at its other end.

One serious problem encountered with a rotary centrifuge seal of the type illustrated in FIG. 1 is illustrated in FIG. 2. Therein, it can be seen that solid particles generated at contact areas between rotatable ceramic ring 26 and fixed graphite ring 28 during operation of centrifuge 10 can fly away from the dynamic seal. Thus, such particles can be projected in many directions and some of these particles can eventually find their way into blood components that have been processed. Thus, it is desirable to minimize the freedom of movement of such particles.

Two ring members of an improved rotary seal according to this invention are shown in FIG. 3. Thus, a rotatable ring member 40 is employed, as well as a non-rotatable ring member 42, and there is an area of contact 44 between rings 40 and 42. The term "non-rotatable" is used in conjunction with ring member 42 in preference to the term "fixed" because, although ring member 42 does remain stationary in normal operation, it is possible in certain embodiments for it to rotate slightly under certain exceptional circumstances prior to attaining a stationary position, as is described below, particularly with reference to FIGS. 9 and 10.

Non-rotatable ring member 42 has, however, been modified to provide increased protection against contamination of blood components with particulate matter generated by the rotary seal. This is achieved by providing an area of non-contact 46 which is located radially inwardly from the area of contact 44. This area of non-contact 46 can be formed by making a continuous recessed portion in the sealing face of ring 42 which is adjacent to the area of contact 44. A typical clearance between the sealing faces of ring members 40 and 42 at the area of non-contact 46 is 0.005 inches.

The advantages of the rotary seal as shown in FIG. 3 are more specifically illustrated in FIG. 4. Therein, it can be seen that the area of non-contact 46 serves as a means for entrapping solid particles generated in the area of contact 44. One particle is shown for illustration, and this particle is first deflected by the recessed portion in the sealing surface of ring 42 and eventually settles upon the surface of rotatable ring member 40. Since ring member 40 is rotating at high speed during operation of the centrifuge, rotational velocity is imparted to the particle resting on its surface which causes the particle to be centrifugally conveyed back to the area of contact 44. Preferably, the surface of this recessed area is joined to the seal contact area by a section of conical surface 48 which slopes gradually toward the contact surface thus providing easy entry of particles into the region of contact 44. The particle is then ingested in the area of contact 44 and ground to fine particles which are expelled at the outer surface of the dynamic seal where they cannot find their way into blood components which are being processed.

FIG. 5 illustrates an alternative embodiment of an improved rotary centrifuge seal according to this invention. Once again, the seal has a rotatable lower ring 40. It also has a non-rotatable ring 50 which has another configuration adjacent to its sealing surface to entrap particles and redirect them back to the area of contact between the ring members. Thus, a series of decreasingly shallower recessed portions 52, 54 and 56 serve a similar purpose to the single recessed portion shown in FIG. 3.

Figure 6:
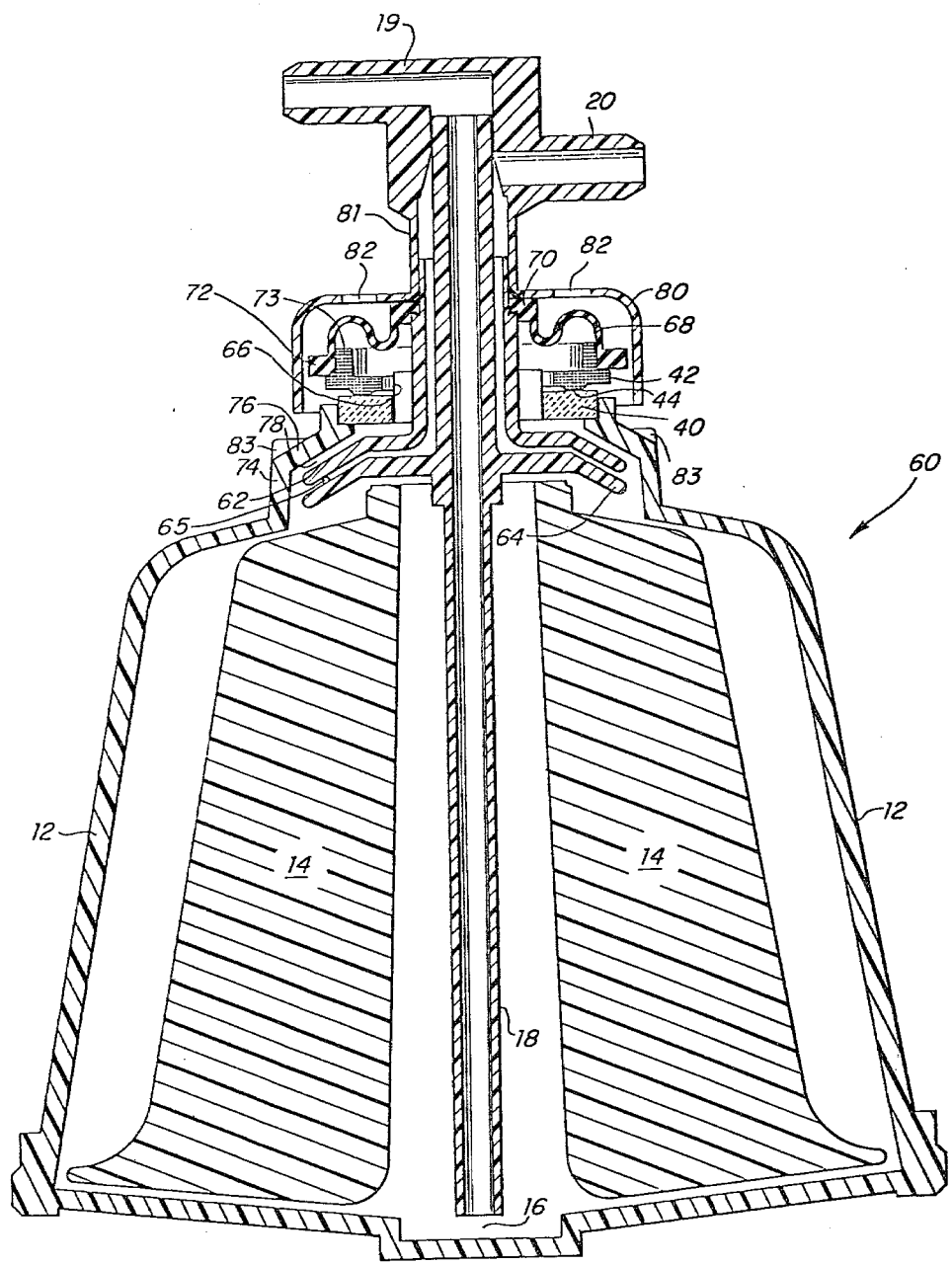
FIG. 6 is a cross-sectional elevational view of a blood-processing centrifuge bowl incorporating an improved rotary seal according to this invention.

FIG. 6 illustrates a blood-processing centrifuge 60 similar but not identical to that of FIG. 1. Similar elements have been given similar numerals for purposes of convenience. Modified centrifuge 60 shown in FIG. 6 operates in a similar manner to centrifuge 10 shown in FIG. 1, except that it has an improved design to minimize particle generation and to entrap and redirect any particles which are generated.

Centrifuge 60 contains an improved rotary seal of the type illustrated in FIGS. 3 and 4. In operation, this rotary seal prevents escape of sterilized gas, such as air, $CO_2$, etc., contained within the closed system and also prevents contamination of the sterilized gas by the external atmosphere.

This improved seal serves to entrap any particles on the blood pathway side generated between the sealing surfaces of lower ceramic rotatable ring 40 and upper non-rotatable graphite ring 42. As discussed above, any particles generated settle upon the shoulder of ring 40 and are then centrifugally conveyed towards the area of contact 44 between rings 40 and 42 where they are ingested, ground to extremely fine particles, and expelled outwardly from the seal so that they do not become entrained in blood being processed.

The rotary seal shown has several additional improvements. One of these is an internal rotating shield 66 which is attached to the inside wall of rotatable ring 40. Shield 66 can be formed from a variety of materials, but a material such as aluminum is preferred because of its light weight and corrosion-resistance properties. Shield 66 adds one more means for preventing solid particles which may be generated from entering blood components being processed.

Resilient diaphragm 68, which can be formed from an elastomeric material, has a lock configuration 70 at its upper end which fits snugly into a keyhole positioned in the upper section of upper channel-defining member 62. Its lower end 72 is designed so that it has to be stretched before it can be slipped over the vertical support 73 on ring member 42; therefore, no adhesive is usually necessary to hold diaphragm 68 over support 73. Adhesives can be used but are usually undesirable since they may run out from the areas in which they are applied thereby providing another possible contaminant within the centrifuge.

The shape and positioning of the respective elements forming the effluent channel for blood components is also improved in centrifuge 60. As shown, the improved rotary seal is positioned a considerable distance away from blood component effluent channel by means of verticle bowl section 74 and inclined bowl section 76. This provides sufficient distance between exiting blood components and the seal rings so that any heat generated at the seal rings will not be in close thermal contact with the blood components. Space 78 provides additional thermal insulation between exiting blood components and the rotary seal.

Both upper and lower channel-defining members 62 and 64 also have an extended diameter. The extended diameter serves to reduce the possibility that blood flowing into central port 16 will flow between inlet tube 18 and cylindrical core 14 thereby by-passing the separation zone in centrifuge 60. The extended diameter chanel-defining members also provide more heat dissipation area in the area of the rotary seal.

Upper channel-defining member 62 is secured at its top end by a slip fit into vertical section 81 of the upper portion of the centrifuge structure. Lower channel-defining member 62 is integrally attached to the upper portion of inlet tube 18, and inlet tube 18 can be joined by an ultrasonic weld to the inner wall of inlet port 19. The proper distance between members 62 and 64 is maintained by protuberances 65.

To further minimize particle generation, generous clearances are provided between rotatable and stationary portions of centrifuge 60. Such generous clearances are particularly desirable: (1) between core 14 and feed tube 18; (2) between shield 66 and member 62; and between shield 66 and fixed graphite ring 42.

Centrifuge 60 is also provided with an external non-rotatable shield 80 which is part of an integral tube section 81. Shield 80 serves to protect the rotary seal from any blows, accidental or deliberate. Such a blow could open the seal thereby destroying the sterility of the system.

To enhance dissipation of heat generated by friction between the dynamic seal faces, air circulation ports 82 in shield 80 and small vanes 83 on rotating bowl 12 are provided, as illustrated. Vanes 83 can be seen more clearly in FIG. 7 and are appropriately sized to obtain good air circulation through the rotary seal without the concomittant disadvantage of creating excessive noise as bowl 12 rotates at high speed.

Figure 8:
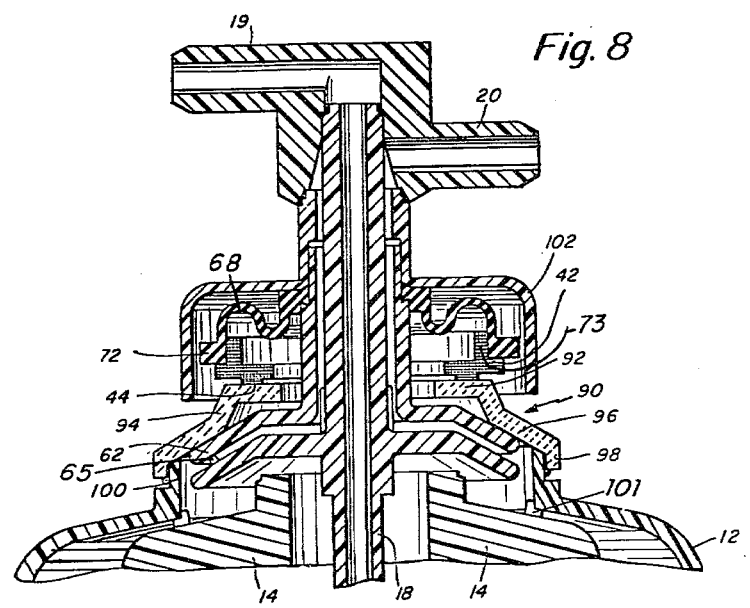
FIG. 8 is a partial cross-sectional elevational view of one alternative embodiment of the improved rotary seal according to this invention.

FIG. 8 illustrates an alternative embodiment of the improved rotary seal shown in a centrifuge similar to that of FIG. 6. Elements which are the same have been numbered consistently with elements of FIG. 6. Rotatable ring member 90 has a more complex shape than in previous embodiments, and includes a horizontally positioned ring portion 92, a steeply downwardly extending portion 94, a less steeply downwardly extending portion 96, and finally a verticle portion 98. Verticle portion 98 can be bonded to a mating surface 100 provided at the top of centrifuge bowl 12. The dynamic seal in this embodiment is formed at the area of contact 44 between the bottom sealing surface of non-rotatable graphite ring 42 and the upper sealing surface of the horizontal ring portion of ring member 90, which is similar to the seal formed by previous embodiments.

Ring member 90 can be formed from a good heat-conducting material, such as a metal, and thus can serve to conduct heat generated in operation away from the area of contact between ring members 42 and 90 to the extended surface areas of ring member 90 where such heat can be dissipated to air currents created as the centrifuge rotates. This prevents the build-up of heat which could result in a temperature rise with concomitant damage to blood components. Because of the excellent heat dissipation obtained through conduction along ring member 90 and subsequent convection to air currents, outer shield 102 need not be provided with air ports for cooling.

As shown, portion 96 of ring member 90 is resting upon upper channel defining member 62. This is the position of these elements when centrifuge 60 stands alone. However, when centrifuge 60 is locked into a chuck of permanent blood-processing apparatus, stationary components of centrifuge 60 are depressed resulting in a separation of member 62 from portion 96.

During normal operating conditions, the improved seal of this invention operates with unusual freedom from noise. This is at least partly due to the fact that the normal torque required to overcome the frictional resistance between the non-rotatable and rotatable ring members is transmitted through the elastomeric diaphragm which forms a secondary seal without any direct physical contact between the non-rotatable ring member and any of the other hard components of the assembly.

Under very exceptional circumstances, the breakaway torque can be greater than the torque capacity of elastomeric diaphragm 68. An example of such exceptional circumstances would be the flooding of the seal with blood followed by a period of non-use sufficient to allow the blood to congeal or form a bond between the non-rotatable and rotatable ring members. This potential problem can be overcome by providing slight modifications to the seal to enable it to momentarily produce the breakaway torque required at start-up without destruction of the seal.

Figure 9:
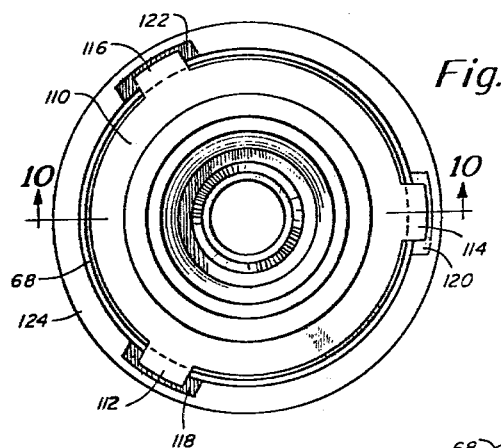
FIG. 9 is a partial cross-sectional view of another alternative embodiment of the improved rotary seal according to this invention; and, FIG. 10 is a cross-sectional view along line 10—10 in FIG. 9.
Figure 10:
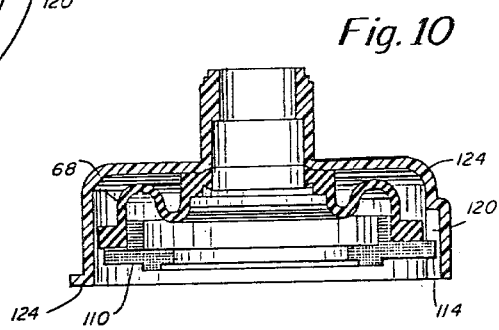

One modification which allows the seal to withstand a higher than normal torque until breakaway is achieved is illustrated in FIGS. 9 and 10. In this embodiment, non-rotatable ring element 110 is provided with three equidistant tabs 112, 114, 116 on its outer periphery. Tabs 112, 114 and 116 extend into complementary recessed areas 118, 120 and 122, respectively, located on the inner surface of outer shield 124. In normal operation, tabs 112, 114 and 116 do not contact shield 124, which avoids wear and the generation of undesirable noise caused by contact between hard components. However, during an exceptional circumstance, where a high breakaway torque is required which exceeds that which can be tolerated by elastomeric diaphragm 68, non-rotatable ring member 110 can rotate just slightly so that tabs 112, 114 and 116 contact the forward edge of recessions 118, 120 and 122, respectively. After such contact is established, torque builds up rapidly until breakaway occurs, after which non-rotatable ring member 110 is returned by the elastic return action of diaphragm 68 to a position where tabs 112, 114 and 116 are once again free floating within their respective recessed portions 118, 120 and 122.

A significant advantage of the improved rotary seal of this invention is the extremely quiet operation which can be achieved. There are several reasons for this, and some of these can be illustrated with reference to FIGS. 8, 9 and 10. As can be seen in FIG. 8, resilient diaphragm 68 terminates in a flange 72 which extends beyond the edge of non-rotatable ring member 42. Thus, if misalignment between rotating and non-rotating parts in the centrifuge occurs, contact is made only between flange 72 and stationary shield 102. Since flange 72 is formed from resilient material, such as an elastomer, there is no significant noise generated by such contact. The only time that there is contact between hard non-rotating and hard rotating elements is in the extreme condition where momentary breakaway torque must be generated by contact of tabs 112, 114 and 116 with the leading edges of recessions 118, 120 and 122, respectively. As soon as the breakaway torque has been achieved, resilient diaphragm 68 returns tabs 112, 114 and 116 to their floating positions within their respective recesses. It should be noted that the inner circumferential wall members of recessions 118, 120 and 122 are spaced sufficiently far from the outer wall surfaces of tabs 112, 114 and 116 so that there is no contact therebetween. Other working clearances are also relatively large so that no hard contact can ever occur under reasonable circumstances.

Those skilled in the art will recognize that there are many equivalents to the specific embodiments described herein. For example, although only two specific designs for the entrapment zone and only one embodiment for the means for providing breakaway torque under exceptional circumstances have been enumerated, a number of other configurations are possible. Such equivalents are intended to be encompassed within the scope of the following claims.

INDUSTRIAL APPLICABILITY

This invention has industrial applicability in clinical laboratories, blood banks, etc., in the separation of blood into two or more components.

I claim:

1. In a rotary centrifuge seal having a lower rotatable ring member and an upper non-rotatable ring member, each of said ring members having a sealing surface thereon to provide a dynamic seal between rotatable elements of a fluid-processing centrifuge and stationary elements of said centrifuge at an area of contact between the sealing surfaces of said ring members:

the improvement comprising providing means for entrapping solid particulate matter generated at the area of contact between said ring members and means for directing entrapped solid particulate matter back to the area of contact between said ring members for ingestion therebetween whereby solid particulate matter generated at the area of contact during operation of said centrifuge is prevented from contaminating fluids processed in the centrifuge.

2. A rotary seal for use in a centrifuge for processing liquids and having rotatable elements including a rotatable bowl, stationary elements, means to admit liquid to said rotatable bowl and means for withdrawing processed liquid, said rotary seal comprising, in combination:

a. a rotatable ring member attached to rotatable elements in said fluid-processing centrifuge, said rotatable ring member having a flat sealing surface thereon;

b. a non-rotatable ring member attached to a stationary element of said centrifuge and positioned above said rotatable ring member, said non-rotatable ring member having a flat sealing surface thereon and being positioned so that there is an area of contact between the sealing surfaces of said rotatable and said non-rotatable ring members, said area of contact establishing a dynamic seal;

c. means for entrapping solid particles generated at said area of contact during operation of the centrifuge; and, d. means for directing entrapped solid particles to said area of contact for ingestion.

3. A seal of claim 2 wherein said rotatable ring member has a smaller inside diameter than said non-rotatable ring member thereby providing a shoulder capable of catching solid particles and imparting rotational velocity to said particles to centrifugally transport said particles toward the area of contact between said first rotatable member and said non-rotatable ring member.

4. A seal of claim 3 wherein said means for entrapping and said means for directing comprise one or more recessions in the sealing face of said non-rotatable ring member, said recessions being positioned adjacently to and radially inwardly of said area of contact between said rotatable and non-rotatable ring members.

5. A seal of claim 4 wherein said rotatable ring member has an extended surface area for dissipating heat and is formed from a good heat-conducting material.

6. A seal of claim 5 additionally including a resilient diaphragm extending between said non-rotatable ring member and a fixed element of said centrifuge, said resilient diaphragm serving as a secondary seal.

7. A seal of claim 6 additionally including means for providing breakaway torque between said rotatable and non-rotatable ring members without significant concomitant buildup of torque on said resilient diaphragm.

8. A seal of claim 7 wherein said means for providing breakaway torque comprises tabs on the periphery of the ring portion of said non-rotatable ring member, said tabs extending into recessed portions of a fixed centrifuge element so that said tabs do not contact the fixed centrifuge element in normal operation but do contact said element if additional torque is required for breakaway in an exceptional circumstance.

9. A seal of claim 8 wherein said resilient diaphragm has a flange thereon which extends beyond the periphery of said non-rotatable ring member whereby the flange will contact said protective shield if misalignment occurs thereby preventing the generation of significant noise caused by contact of hard components.

10. A seal of claim 9 additionally including a protective shield around the exterior of said rotary seal.

11. A seal of claim 10 wherein said non-rotatable ring member has a convex radius at its inside lower corner to facilitate access for loose solid particles into the area of contact between said ring members.

12. A seal of claim 11 additionally including a cylindrical rotatable shield positioned inside the rotatable and non-rotatable ring members and projecting above the plane of the rubbing surfaces to deflect loose particles impinging thereon towards the area of contact between said ring members.

13. The rotary seal of claim 2 in which the rotatable ring member is adapted to be directly affixed to a mating surface at the top of the rotatable bowl.

14. In a blood processing centrifuge having rotatable elements including a rotatable bowl, stationary elements, means to admit blood to said rotatable bowl and means for withdrawing blood components from said bowl, a rotary seal including a rotatable ring member attached to a rotatable element of said blood centrifuge and positioned beneath a non-rotatable ring member attached to a stationary element of said blood centrifuge, and a resilient diaphragm extending between said non-rotatable ring member and a fixed element of said centrifuge:

the improvement comprising additionally including means for providing breakaway torque between said rotatable and non-rotatable ring members without significant concomitant buildup of torque on said resilient diaphragm.

15. An improvement of claim 14 wherein said means for providing breakaway torque comprises tabs on the periphery of the ring portion of said non-rotatable ring member, said tabs extending into recessed portions of a fixed centrifuge element so that said tabs do not contact the fixed centrifuge element in normal operation but do contact said element if additional torque is required for breakaway in an exceptional circumstance.

16. An improvement of claim 15 wherein said resilient diaphragm has a flange thereon which extends beyond the periphery of said non-rotatable ring member whereby the flange will contact said protective shield if misalignment occurs thereby preventing the generation of significant noise caused by contact of hard components.

17. An improvement of claim 14 wherein the rotatable ring member includes a portion which is adapted to be directly affixed to a mating surface at the top of the bowl.

* * * * *